United States Patent
Lei (10) Patent No.: US 11,672,665 B2
(45) Date of Patent: Jun. 13, 2023

(54) PAD FOR ACETABULAR BONE REVISION AND RECONSTRUCTION AND FIXING STRUCTURE FOR PAD AND ACETABULAR CUP PROSTHESIS

(71) Applicant: THE THIRD HOSPITAL OF CHANGSHA, Changsha (CN)

(72) Inventor: Qing Lei, Changsha (CN)

(73) Assignee: THE THIRD HOSPITAL OF CHANGSHA, Changsha (CN)

( * ) Notice: Subject to any disclaimer, the term of this patent is extended or adjusted under 35 U.S.C. 154(b) by 0 days.

(21) Appl. No.: 17/817,683

(22) Filed: Aug. 5, 2022

(65) Prior Publication Data
US 2023/0143834 A1    May 11, 2023

(30) Foreign Application Priority Data
Nov. 10, 2021 (CN) .......................... 202111329391.8

(51) Int. Cl.
*A61F 2/34* (2006.01)
*A61F 2/30* (2006.01)

(52) U.S. Cl.
CPC ............ *A61F 2/34* (2013.01); *A61F 2/30734* (2013.01); *A61F 2/30965* (2013.01); *A61F 2002/30387* (2013.01); *A61F 2220/0025* (2013.01); *A61F 2310/00952* (2013.01)

(58) Field of Classification Search
CPC ..................................... A61F 2/32; A61F 2/34
See application file for complete search history.

(56) References Cited

U.S. PATENT DOCUMENTS

| 6,290,727 | B1 * | 9/2001 | Otto ..................... A61F 2/30724 623/22.21 |
| 2008/0021568 | A1 | 1/2008 | Tulkis et al. |
| 2012/0221115 | A1 * | 8/2012 | Komistek ................ A61F 2/34 29/592 |

FOREIGN PATENT DOCUMENTS

CN          206651895 U          11/2017

OTHER PUBLICATIONS

First Office Action dated Jun. 9, 2022, in connection with Chinese Patent Application No. 202111329391.8, 13 pgs. (including translation).

* cited by examiner

*Primary Examiner* — Jason-Dennis N Stewart
(74) *Attorney, Agent, or Firm* — Chiesa, Shahinian & Giantomasi PC (57) ABSTRACT

The present disclosure relates to the field of medical instruments, in particular to a pad for acetabular bone revision and reconstruction and a fixing structure for a pad and an acetabular cup prosthesis. The pad is located between an acetabular cup prosthesis and the acetabular bone, and is connected to the acetabular cup prosthesis and the acetabular bone respectively. The pad includes a first component and a second component which has the same or different radius and shape as or from the radius and shape of the first component; the first component is movably connected with the second component; and the shape of the connected first component and second component is matched with a defective part of the acetabular bone.

14 Claims, 7 Drawing Sheets

PAD FOR ACETABULAR BONE REVISION AND RECONSTRUCTION AND FIXING STRUCTURE FOR PAD AND ACETABULAR CUP PROSTHESIS

CROSS REFERENCE TO RELATED APPLICATION

This application claims priority from Chinese Patent Application No. 202111329391.8, filed Nov. 10, 2021, the disclosure of which is incorporated herein by reference in its entirety as part of the present application.

FIELD

The present disclosure relates to the field of medical instruments, in particular to a pad for acetabular bone revision and reconstruction and a fixing structure for a pad and an acetabular cup prosthesis.

BACKGROUND

The current methods for reconstructing acetabular bone defects include compression bone grafting, structural bone grafting, jumbo cup, reinforcing ring, cup-cage, 3D printing of a personalized acetabular cup prosthesis, etc. Using an allogeneic bone to treat a large-area bone defect cannot achieve good initial stability, so that prosthesis loosening and bone resorption are prone to occur. Kostensalo et al. reported 60 cases of hip joint revisions using a combination of the compression bone grafting and a cement cup. The patients were visited for averagely 7 years. An average survival rate was 73% if a second revision is taken as the end of the life. 13 of the 60 cases belong to aseptic loosening, which accounts for 81%.

It has been reported that whether it is an autologous or allogeneic large structural grafted bone, in a process of bone fusion, bone healing occurs only at a few millimeters from an outer layer of the grafted bone, while osteonecrosis remains in the center of the grafted bone. This leads to the collapse, resorption, and displacement of the grafted bone, which eventually leads to a failure of the revision.

The use of the Jumbo cup can reduce the use of a grafted bone. A center of rotation is moved outwards and downwards as far as possible to be close to an anatomical position, but a large Jumbo cup is not conducive to the recovery of bone mass, and makes it more difficult to second revision. Since good initial stability cannot be achieved, large anteroposterior columns and external upper bone defects limit the use of the large Jumbo cup.

The design of a metal porous structure is conducive to bone ingrowth, and its excellent friction coefficient is conducive to better original press-fitting, so as to provide good conditions for the initial stability and long-term stability of a prosthesis. The metal porous structure has been widely used in bone defect repair in the hip joint revision and achieves a good effect.

In the related art, a reconstruction method for repairing an acetabular bone defect using the design of a metal porous structure is generally used in combination with the pad. The pad is used to fill a defective part of an acetabular bone. The pad currently used on the market is of an integrated structure and a single type, is thicker, cannot reconstruct and fix bone defects with different shapes, and is poor in adaptability.

In view of the above-mentioned related technologies, the prior art discloses pads with an integrated structure, that cannot reconstruct and fix acetabular bones of different shapes, and have poor adaptability.

SUMMARY

The present invention provides a pad for acetabular bone revision and reconstruction and a fixing structure for a pad and an acetabular cup prosthesis.

In a first aspect, the present disclosure provides a pad for acetabular bone revision and reconstruction. The following technical solutions are adopted:

A pad for acetabular bone revision and reconstruction is provided. The pad is located between an acetabular cup prosthesis and the acetabular bone, and is connected to the acetabular cup prosthesis and the acetabular bone respectively; the pad includes a first component and a second component which has the same or different radius and shape as or from the radius and shape of the first component; the first component is movably connected with the second component; and the shape of the connected first component and second component is matched with a defective part of the acetabular bone.

The first component and the second component, which have the same or different radiuses and shapes, are movably connected, and the shape of their combination is matched with the shape of the defective part of the acetabular bone. Thus, more effectively repairing the defective part of the acetabular bone. The first component and the second component are applicable to acetabular bone defects with different shapes to better reconstruct and fix the acetabular bone, facilitate subsequent fixing of an acetabular cup prosthesis; and the split structure of the pad improves operation flexibility.

Optionally, the first component and the second component are of a ¼ or ⅛ spherical shape; thicknesses of the first component or the second component are uniformly and consistent, or the first component or the second component have thin edges and are gradually thickened towards a sphere center position, or have thick edges and are gradually thinned towards a sphere center position.

The shape and degree of wear of a defective part of the acetabular bone of each patient are different. Thus, it is necessary to prepare pads of different specifications to meet the needs of different patients. According to the designed pad, a first component and a second component which have the same thicknesses and the same radiuses can be combined and connected, and a first component and a second component which have different thicknesses and different radiuses can also be combined and connected. Combinations in different forms can be better applied to the acetabular bone defects of different patients, thus improving the comfort of the pad.

Optionally, a side wall of the first component or the second component is provided with a dovetail groove; a side wall of the second component or the first component is provided with a dovetail block used cooperatively with the dovetail groove; and the first component and the second component are movably connected through clamping between the dovetail groove and the dovetail block.

Additionally, the first component and the second component are connected through clamping between the dovetail groove and the dovetail block, so that the flexibility of operation of the pad is improved, and the working efficiency is also improved.

Optionally, the invention also comprises a length of a bottom surface of the dovetail groove that gradually decreases from the side close to the acetabular cup prosthesis to the side away from the acetabular bone; a longitudinal section of the dovetail groove is a frustum; a side surface of the dovetail block close to the bottom surface of the dovetail groove gradually decreases from the side close to the acetabular cup prosthesis to the side away from the acetabular bone; and a longitudinal section of the dovetail block is a frustum.

In another embodiment, the longitudinal sections of both of the dovetail groove and the dovetail block are the frustums, so that after they are clamped with each other, the dovetail block can be limited in an insertion direction to prevent the dovetail block from being separated from the dovetail groove in the insertion direction during insertion, thus defining that the dovetail groove and the dovetail block can only be separated from each other in one direction. Therefore, the degrees of freedom of the first component and the second component are restrained in a left direction, a right direction and a downward direction, and the firmness between the first component and the second component is guaranteed.

Optionally, a plurality of oblong mounting holes are formed in each of the first component and the second component; screws are inserted into the mounting holes, and a gap is reserved between the screws; and the first component and the second component are fixedly connected to the acetabular bone by inserting the screws into the mounting holes.

By adopting the above-mentioned technical solution, after the screws are inserted into the mounting holes, the screws can move up, down, left and right in the mounting holes. Since the screws need to be fixed at a thicker position on the acetabular bone, the screws can be fixed at proper positions on the acetabular bone by moving the positions of the screws in the mounting holes, so as to ensure the stability between the acetabular bone and the first component as well as the second component.

In a another aspect, the present disclosure provides a fixing structure for a pad and an acetabular cup prosthesis. The following technical solution is adopted.

In the fixing structure for the pad and the acetabular cup prosthesis, a plurality of circular slots are formed in each of the first component and the second component; a side surface of the acetabular cup prosthesis close to the pad is coated with bone cement; the first component and the second component are in contact with the acetabular cup prosthesis; and the first component and the second component are fixedly connected to the acetabular cup prosthesis by enabling the bone cement to enter the plurality of circular slots.

By adopting the above-mentioned technical solution, the bone cement coated on the acetabular cup prosthesis enters the plurality of circular slots, so that the engomphosis force between the bone cement and the pad is enhanced, thus improving the stability between the pad and the acetabular cup prosthesis.

Optionally, side surfaces of the first component and the second component close to the acetabular cup prosthesis are provided with cover layers, and notches of the circular slots are formed in the cover layers.

By adopting the above-mentioned technical solution, the engomphosis force between the bone cement and the pad is enhanced, so that the first component and the second component are fixedly connected to the acetabular cup prosthesis to effectively avoid the problem of pad loosening caused by collapse and resorption of a grafted bone and also avoid an extremely high shear force caused by fixing the acetabular cup prosthesis on the pad with the bone cement.

In conclusion, the present disclosure includes at least one of the following beneficial technical effects:

First, in the present disclosure, the first component and the second component which have the same or different radiuses and shapes are movably connected, and the shape of their combination is matched with the shape of the defective part of the acetabular bone, thus better repairing the defective part of the acetabular bone. The present disclosure is applicable to acetabular bone defects with different shapes to better reconstruct and fix the acetabular bone and facilitate subsequently fixing the acetabular cup prosthesis; and the split structure of the pad improves the operation flexibility.

Secondly, in the present disclosure, the bone cement coated on the acetabular cup prosthesis enters the plurality of circular slots, so that the engomphosis force between the bone cement and the pad is enhanced, thus improving the stability between the pad and the acetabular cup prosthesis.

Reference numerals in the drawings: 1: first component; 2: second component; 3: dovetail groove; 4: dovetail block; 5: mounting hole; 6: circular slot; 7: cover layer; 8: porous structural layer.

DETAILED DESCRIPTION OF THE EMBODIMENTS

The present disclosure is further described in detail below in combination with accompanying drawings 1-7.

Embodiments of the present disclosure disclose a pad for acetabular bone revision and reconstruction and a fixing structure for a pad and an acetabular cup prosthesis.

Embodiment I

Figure 1:
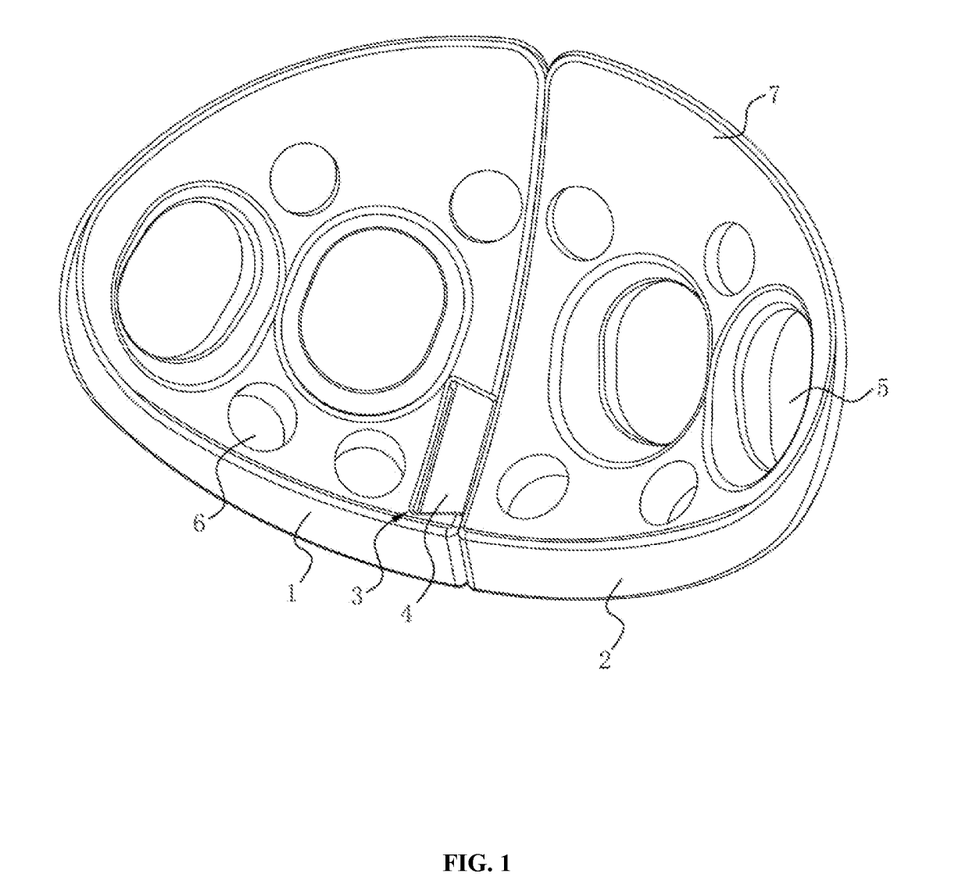
FIG. 1 is a schematic structural diagram of Embodiment I.

Referring to FIG. 1, a pad for acetabular bone revision and reconstruction is located between an acetabular cup prosthesis and the acetabular, and is connected to the acetabular cup prosthesis and the acetabular bone respectively. The pad includes a first component 1; a second component 2 is clamped on the first component 1. The first component 1 and the second component 2 are of a ⅛ spherical shape. The radius and shape of the first component 1 are the same as those of the second component 2. For the thickness, each of the first component 1 and the second component 2 has a thin edge and is gradually thickened towards a sphere center position. The edges of the first component 1 and the second component 2 extend into the acetabular bone. The shape of the clamped first component 1 and the second component 2 is of a ¼ spherical shape; and the shape and thickness of the clamped first component 1 and the second component 2 adapt to a defective part of the acetabular bone.

Figure 2:
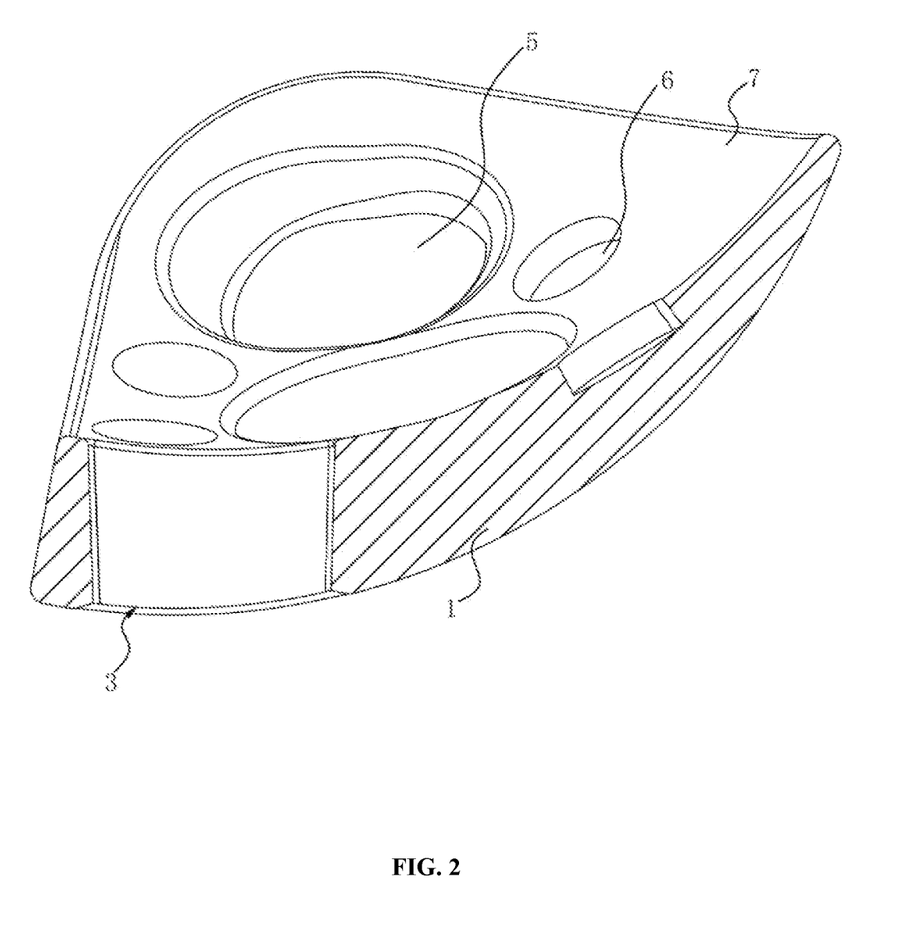
FIG. 2 is a sectional view of a dovetail groove in a first component of Embodiment I.
Figure 3:
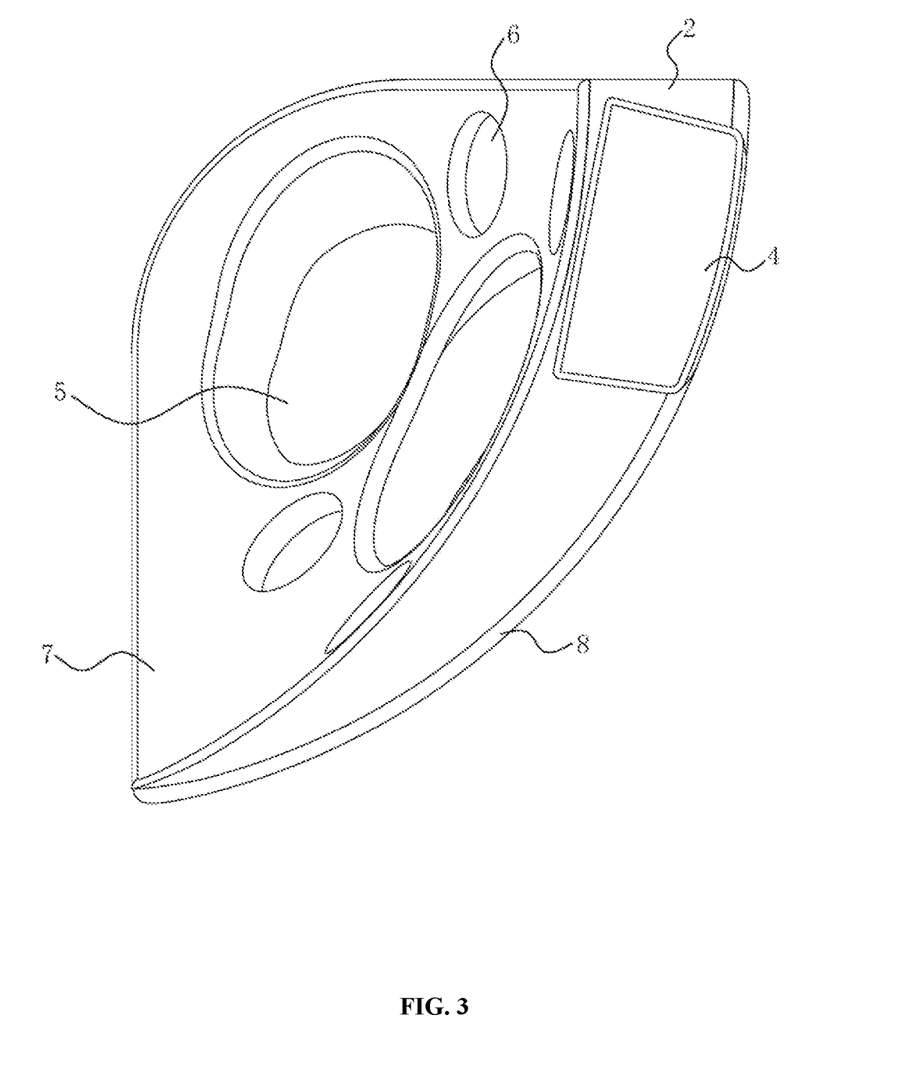
FIG. 3 is a schematic structural diagram of a dovetail block in a second component of Embodiment I.

Referring to FIG. 2 and FIG. 3, a side wall of the first component 1 close to the second component 2 is provided with a dovetail groove 3, and a side wall of the second component 2 close to the first component 1 is provided with a dovetail block 4. The dovetail block 4 and the dovetail groove 3 are clamped with each other to connect the first component 1 to the second component 2.

A length of a bottom surface of the dovetail groove 3 gradually decreases from one side close to the acetabular cup prosthesis to one side away from the acetabular bone; a longitudinal section of the dovetail groove 3 is a frustum; a side surface of the dovetail block 4 close to the bottom surface of the dovetail groove 3 gradually decreases from the side close to the acetabular cup prosthesis to the side away from the acetabular bone; and a longitudinal section of the dovetail block (4) is a frustum. The frustum shape enables the dovetail block 4 and the dovetail groove 3 to be gradually tightened. After the dovetail block 4 is inserted into the dovetail groove 3 in a direction close to the acetabular cup prosthesis, the dovetail block 4 is prevented from being separated from the dovetail groove 3.

A plurality of mounting holes 5 are formed in the first component 1 and the second component 2. The mounting holes 5 are counterbores. The first component 1 and the second component 2 are fixedly connected to the acetabular bone in a manner of inserting screws into the mounting holes 5. The mounting holes 5 are oblong. After the screws are inserted into the mounting holes 5, due to the shape of the mounting holes 5, gaps are served between the screws and hole walls of the mounting holes 5, so that the screws can move in the mounting holes 5, and the screws are adjusted to be fixed at thicker positions on the acetabular bone.

In the fixing structure for a pad and an acetabular cup prosthesis, side surfaces of the first component 1 and the second component 2 close to the acetabular cup prosthesis are provided with cover layers 7. The first component 1 and the second component 2 are of bone trabecula structures, and the cover layers 7 are solid layers.

A plurality of circular slots 6 are formed in the cover layers 7, the first component 1 and the second component 2 close to the acetabular cup prosthesis. Side surfaces of the acetabular cup prosthesis close to the first component 1 and the second component 2 are coated with one layer of bone cement. After the acetabular cup prosthesis is put into a recess formed by the first component 1 and the second component 2, the bone cement on the acetabular cup prosthesis enters the plurality of circular slots 6. The bone cement entering the circular slots 6 is formed into a bone cement column, so that the first component 1 and the second component 2 can be fixedly connected to the acetabular cup prosthesis. The depth of the circular slots 6 increases as the thickness of the first component 1 or the second component 2 gradually increases.

The first component 1 and the second component 2 cannot be fixed to the acetabular cup prosthesis directly through the bone cement. Since gaps of the bone trabecula are different in size, it is hard for the bone cement to penetrate into the gaps of the bone trabecula, or the engomphosis force between the bone cement that penetrates into the gaps of the bone trabecula and the gaps is poor, and the formed connection is weak, resulting in that the first component 1 and the second component 2 cannot be fixedly connected to the acetabular cup prosthesis. Therefore, by the arrangement of the cover layers 7, the bone cement is prevented from penetrating into the gaps of the bone trabecula, but can directly enter the circular slots 6.

The implementation principle of Embodiment I is as follows: The first component 1 and the second component 2 are clamped and put to the defective part of the acetabular bone; the screws are inserted into the mounting holes 5 and into the acetabular cup prosthesis to fixedly connect the first component 1 and the second component 2 to the acetabular cup prosthesis; the side surface of the acetabular cup prosthesis is then coated with one layer of bone cement; the acetabular cup prosthesis is put into the recess formed by the first component 1 and the second component 2; the bone cement enters the circular slots and is then cured to complete connection of the pad to the acetabular cup prosthesis and the acetabular bone.

Embodiment II

Figure 4:
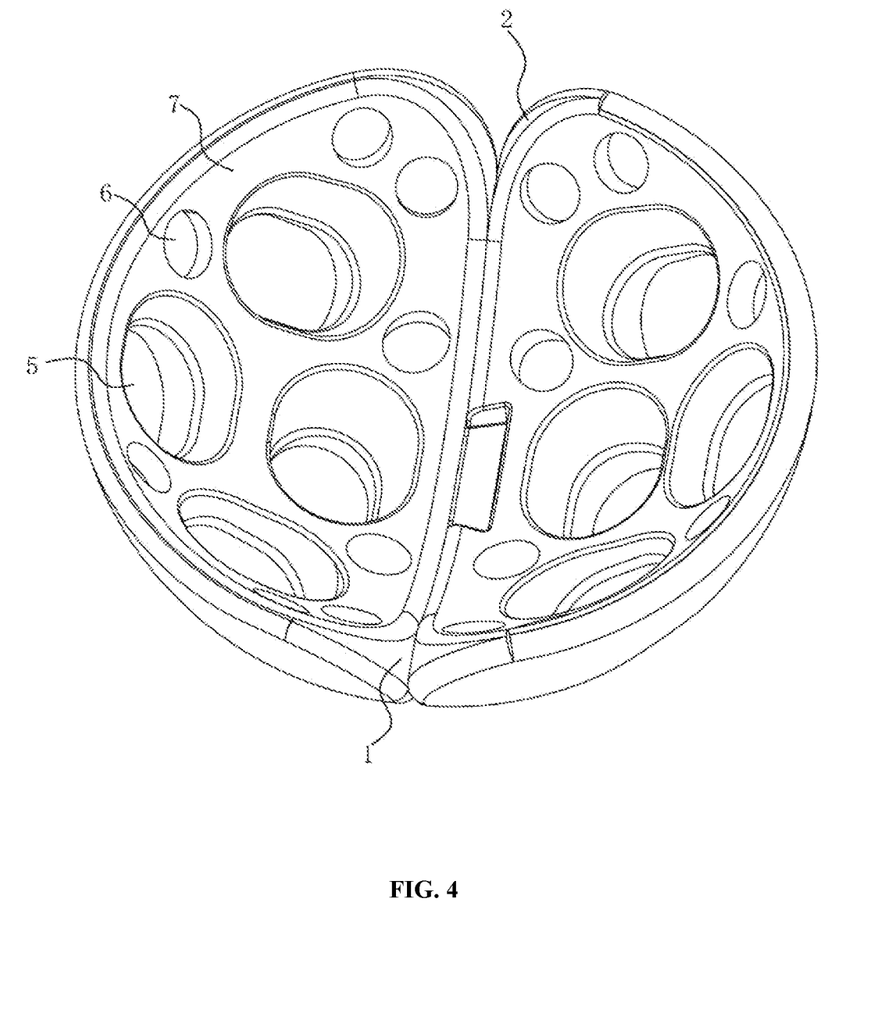
FIG. 4 is a schematic structural diagram of Embodiment II.

Referring to FIG. 4, the first component 1 and the second component 2 are of a ¼ spherical shape. The radius and shape of the first component 1 are the same as those of the second component 2. For the thickness, each of the first component 1 and the second component 2 has a thin edge and is gradually thickened towards a sphere center position. The shape of the clamped first component 1 and the second component 2 is of a semi-spherical shape; and the shape and thickness of the clamped first component 1 and the second component 2 adapt to a defective part of the acetabular bone.

Figure 5:
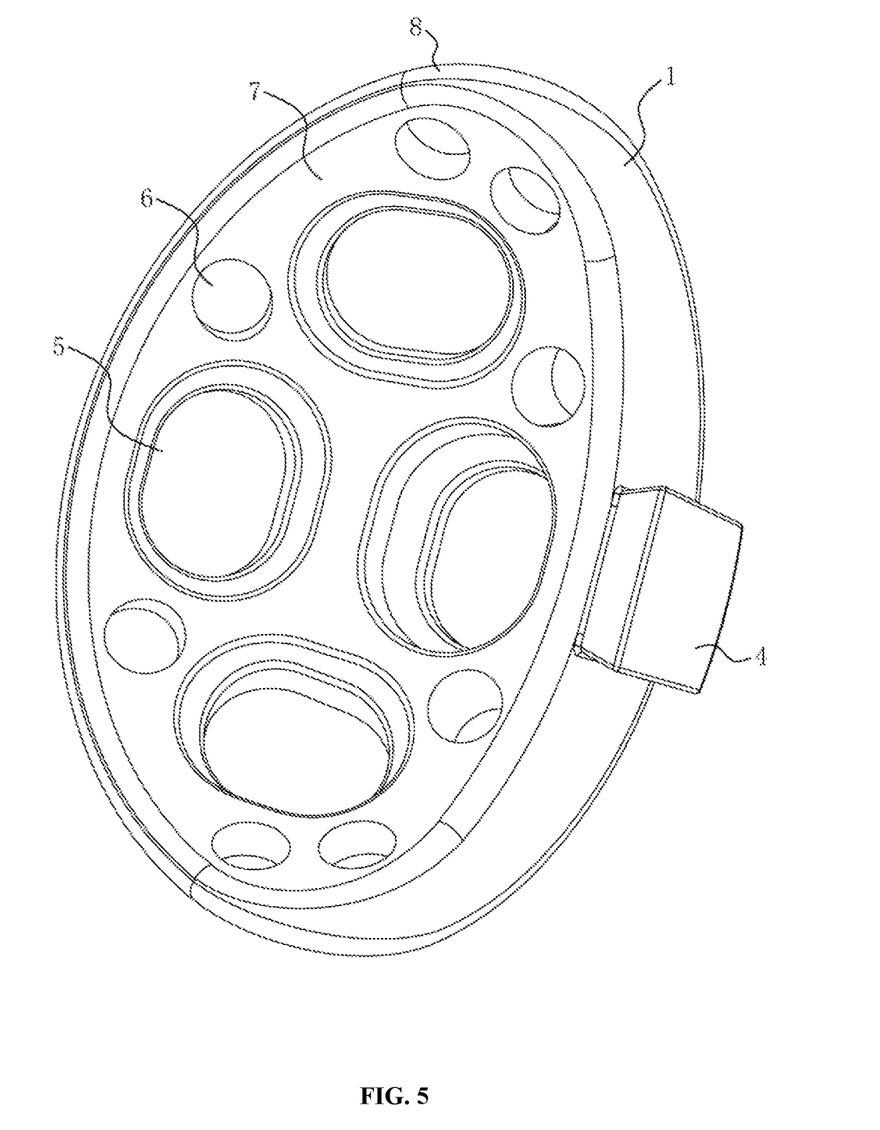
FIG. 5 is a schematic structural diagram of a dovetail block in a first component of Embodiment II.
Figure 6:
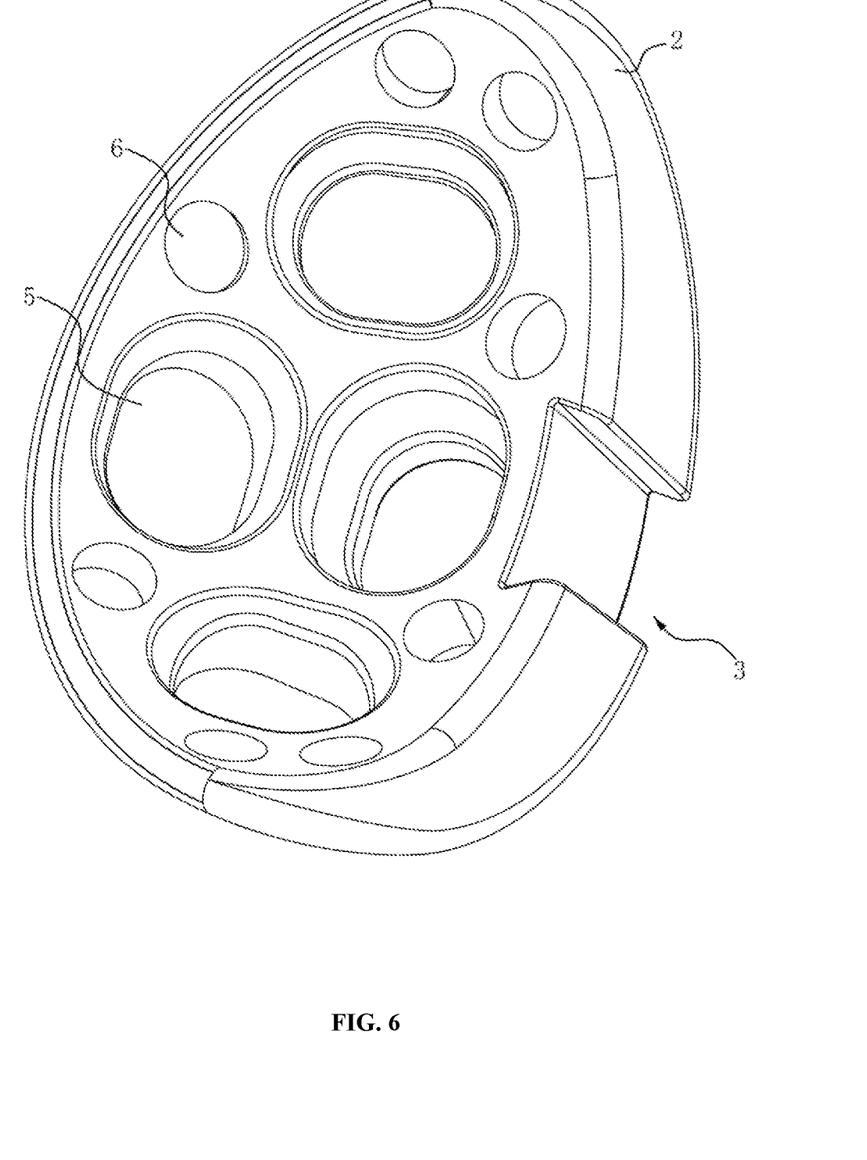
FIG. 6 is a schematic structural diagram of a dovetail groove in a second component of Embodiment II.

Referring to FIG. 5 and FIG. 6, a side wall of the first component 1 close to the second component 2 is provided with a dovetail block 4, and a side wall of the second component 2 close to the first component 1 is provided with a dovetail groove 3. The dovetail block 4 and the dovetail groove 3 are clamped with each other to connect the first component 1 to the second component 2.

Figure 7:
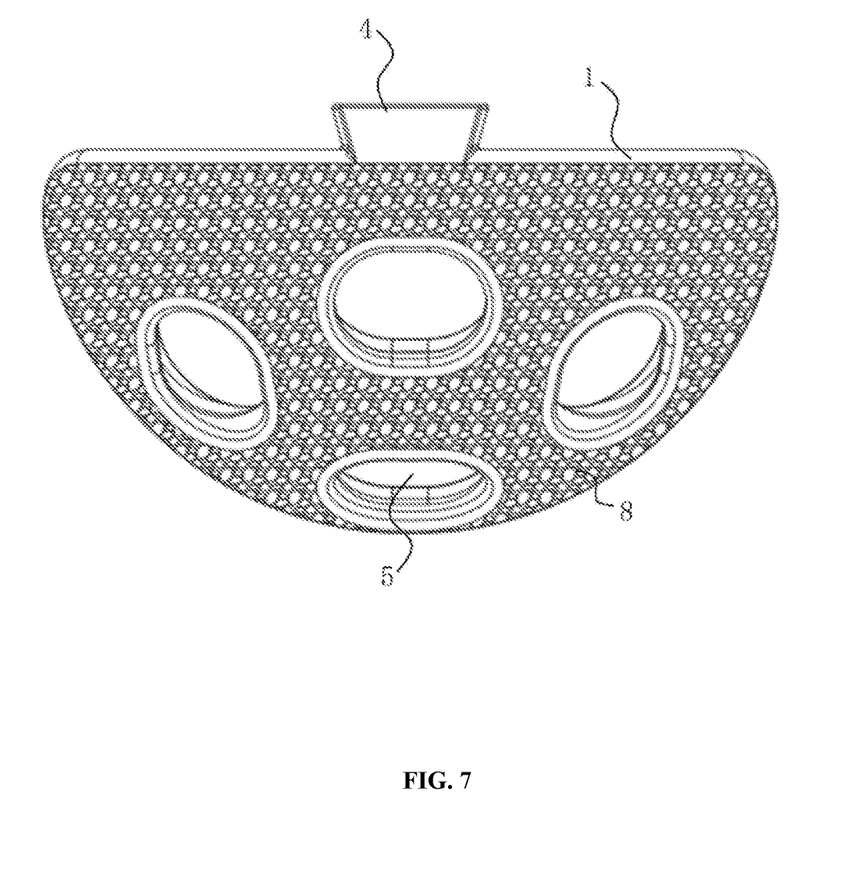
FIG. 7 is a schematic structural diagram of a porous structural layer in a first component of Embodiment II.

Referring to FIG. 7, side surfaces of the first component 1 and the second component 2 close to the acetabular bone are provided with a porous structural layer 8 that imitates a cancellous bone, which is conductive to the bone ingrowth of the acetabular bone in the acetabular cup prosthesis. The excellent friction coefficient of the porous structural layer is favorable for better original press-fitting, which provides good conditions for initial stability and long-term stability of the acetabular cup prosthesis. The porosity of 60%-80% of the porous structural layer 8 is conductive to the ingrowth of bone tissues; crosslinked micro structures are formed to achieve a long-term biological fixing effect; and the service life of the acetabular cup prosthesis is prolonged.

The implementation principle of Embodiment II is the same as that of Embodiment I, which will not be repeatedly described here.

In addition to the above two embodiments, the first component 1 and the second component 2 may adopt the following combination modes according to the defective condition of the acetabular bone:

(1) A first component 1 and a second component 2 which are uniform and consistent in thickness and have the same radiuses are selected to be combined;

or (2) a first component 1 and a second component 2 which are uniform and consistent in thickness and have different radiuses are selected to be combined;

or (3) a first component 1 which is uniform and consistent in thickness, and a second component 2 which has a thick edge, is gradually thinned towards a sphere center position and has the same radius as that of the first component 1 are selected to be combined;

or (4) a first component 1 which is uniform and consistent in thickness, and a second component 2 which has a thick edge, is gradually thinned towards a sphere center position and has a radius different from that of the first component 1 are selected to be combined;

or (5) a first component 1 and a second component 2 which both have thick edges, are gradually thinned towards a sphere center position and have the same radiuses are selected to be combined;

or (6) a first component 1 and a second component 2 which both have thick edges, are gradually thinned towards a sphere center position and have different radiuses are selected to be combined.

The preferred embodiments of the present disclosure are herein, and are not intended to limit the scope of the present disclosure or patent claims. Therefore, any equivalent changes made according to the structure, shape and principle of the present disclosure shall all fall within the protection scope of the present disclosure.

What is claimed is:

1. A pad for acetabular bone revision and reconstruction, the pad comprises:
    a first component with a shape and radius; and
    a second component which with a shape and radius; the first component being movably connected with the second component; and the shape of the connected first component and the shape of the second component are each of a ¼ or ⅛ spherical shape, wherein thicknesses of the first component and the second component are uniform and consistent, or the first component and the second component have thin edges and are gradually thickened towards a sphere center position, or the first component and the second component have thick edges that are gradually thinned towards a sphere center position.

2. The pad for acetabular bone revision and reconstruction according to claim 1, wherein a side wall of the first component or the second component is provided with a dovetail groove; and a side wall of the second component or the first component is provided with a dovetail block to cooperate with the dovetail groove; and the first component and the second component are movably connected by clamping the dovetail groove and the dovetail block.

3. The pad for acetabular bone revision and reconstruction according to claim 2, wherein
    the dovetail groove of the first component is recessed from the side wall of the first component towards a sphere center of the first component, and the dovetail groove comprises a first bottom wall and two first side walls arranged in a longitudinal direction of the first component, a distance between the two first side walls gradually decreases along a height direction of the dovetail groove of the first component away from the first bottom wall, and a longitudinal section of the dovetail groove of the first component is a frustum; and
    a dovetail block of the second component protrudes from the side wall of the second component, and the dovetail block comprises second side parts and a second top part, wherein a distance between two second side parts of the second side parts arranged along a longitudinal direction of the second component gradually decreases along a height direction of the dovetail block of the second component away from the second top part, and a longitudinal section of the dovetail block of the second component is a frustum;
    or
    the dovetail groove of the second component is recessed from the side wall of the second component towards a sphere center of the second component, and the dovetail groove comprises a second bottom wall and two second side walls arranged in a longitudinal direction of the second component, a distance between the two second side walls gradually decreases along a height direction of the dovetail groove of the second component away from the second bottom wall, a longitudinal section of the dovetail groove of the second component is a frustum; and
    a dovetail block of the first component protrudes from the side wall of the first component, and the dovetail block comprises first side parts and a first top part, wherein a distance between two first parts of the first side parts arranged along a longitudinal direction of the first component gradually decreases along a height direction of the dovetail block of the first component away from the first top part, and a longitudinal section of the dovetail block of the first component is a frustum.

4. The pad for acetabular bone revision and reconstruction according to claim 3, wherein the pad has a plurality of oblong mounting holes in each of the first component and the second component; said holes are designed for screws to be inserted into the holes, and a gap is reserved between one of the screws and a corresponding one of the holes.

5. A fixing structure for the pad according to claim 1, and an acetabular cup prosthesis, wherein a plurality of circular slots are formed in each of the first component and the second component; a side surface of the acetabular cup prosthesis close to the pad is coated with bone cement; the first component and the second component are in contact with the acetabular cup prosthesis; and the first component and the second component are fixedly connected to the acetabular cup prosthesis by bone cement entering the plurality of circular slots.

6. The fixing structure for the pad and the acetabular cup prosthesis according to claim 5, wherein side surfaces of the first component and the second component close to the acetabular cup prosthesis are provided with cover layers, and notches of the circular slots are formed in the cover layers.

7. The fixing structure for the pad and the acetabular cup prosthesis according to claim 5, wherein the first component and the second component are of a ¼ or ⅛ spherical shape; thicknesses of the first component and the second component are uniformly and consistent, or the first component and the second component have thin edges and are gradually thickened towards a sphere center position, or have thick edges and are gradually thinned towards a sphere center position.

8. The fixing structure for the pad and the acetabular cup prosthesis according to claim 7, wherein side surfaces of the first component and the second component close to the acetabular cup prosthesis are provided with cover layers, and notches of the circular slots are formed in the cover layers.

9. The fixing structure for the pad and the acetabular cup prosthesis according to claim 7, wherein a side wall of the first component or the second component is provided with a dovetail groove; a side wall of the second component or the first component is provided with a dovetail block used cooperatively with the dovetail groove; and the first component and the second component are movably connected by clamping the dovetail groove and the dovetail block.

10. The fixing structure for the pad and the acetabular cup prosthesis according to claim 9, wherein side surfaces of the first component and the second component close to the acetabular cup prosthesis are provided with cover layers, and notches of the circular slots are formed in the cover layers.

11. The fixing structure for the pad and the acetabular cup prosthesis according to claim 9, wherein the dovetail groove of the first component is recessed from the side wall of the first component towards a sphere center of the first component, and the dovetail groove comprises a first bottom wall and two first side walls arranged in a longitudinal direction of the first component, a distance between the two first side walls gradually decreases along a height direction of the dovetail groove of the first component away from the first bottom wall; and
a longitudinal section of the dovetail groove of the first component is a frustum;
a dovetail block of the second component protrudes from the side wall of the second component, and the dovetail block comprises second side parts and a second top part, wherein a distance between two second side parts of the second side parts arranged along a longitudinal direction of the second component gradually decreases along a height direction of the dovetail block of the second component away from the second top part, and a longitudinal section of the dovetail block of the second component is a frustum;
or
the dovetail groove of the second component is recessed from the side wall of the second component towards a sphere center of the second component, and the dovetail groove comprises a second bottom wall and two second side walls arranged in a longitudinal direction of the second component, a distance between the two second side walls gradually decreases along a height direction of the dovetail groove of the second component away from the second bottom wall, a longitudinal section of the dovetail groove of the second component is a frustum; and
a dovetail block of the first component protrudes from the side wall of the first component, and the dovetail block comprises first side parts and a first top part, wherein a distance between two first parts of the first side parts arranged along a longitudinal direction of the first component gradually decreases along a height direction of the dovetail block of the first component away from the first top part, and a longitudinal section of the dovetail block of the first component is a frustum.

12. The fixing structure for the pad and the acetabular cup prosthesis according to claim 11, wherein side surfaces of the first component and the second component close to the acetabular cup prosthesis are provided with cover layers, and notches of the circular slots are formed in the cover layers.

13. The fixing structure for the pad and the acetabular cup prosthesis according to claim 11, wherein the pad has a plurality of oblong mounting holes in each of the first component and the second component; said holes are designed to insert screws into the mounting holes, and a gap is reserved between one of the screws and a corresponding one of the holes.

14. The fixing structure for the pad and the acetabular cup prosthesis according to claim 13, wherein side surfaces of the first component and the second component close to the acetabular cup prosthesis are provided with cover layers, and notches of the circular slots are formed in the cover layers.

\* \* \* \* \*